(12) United States Patent
Freiman et al.

(10) Patent No.: US 11,361,432 B2
(45) Date of Patent: Jun. 14, 2022

(54) INFLAMMATION ESTIMATION FROM X-RAY IMAGE DATA

(71) Applicant: KONINKLIJKE PHILIPS N.V., Eindhoven (NL)

(72) Inventors: Mordechay Pinchas Freiman, Zichron-Yaakov (IL); Liran Goshen, Zichron-Yaakov (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/632,420

(22) PCT Filed: Jul. 19, 2018

(86) PCT No.: PCT/EP2018/069616
§ 371 (c)(1),
(2) Date: Jan. 20, 2020

(87) PCT Pub. No.: WO2019/016309
PCT Pub. Date: Jan. 24, 2019

(65) Prior Publication Data
US 2020/0226749 A1    Jul. 16, 2020

(30) Foreign Application Priority Data
Jul. 19, 2017  (EP) .................................. 17182117

(51) Int. Cl.
*G06T 7/00*      (2017.01)
*A61B 6/03*      (2006.01)
(Continued)

(52) U.S. Cl.
CPC ............ *G06T 7/0012* (2013.01); *A61B 6/032* (2013.01); *A61B 6/504* (2013.01); *A61B 6/5217* (2013.01);
(Continued)

(58) Field of Classification Search
None
See application file for complete search history.

(56) References Cited

U.S. PATENT DOCUMENTS 4,945,478 A * 7/1990 Merickel ................ A61B 5/055
382/131
2008/0009702 A1    1/2008 Liu
(Continued)

FOREIGN PATENT DOCUMENTS

JP      2011218037 A    11/2011
JP       5484998 B2      5/2014
(Continued)

OTHER PUBLICATIONS

PCT International Search Report, International application No. PCT/EP2018/069616, dated Oct. 17, 2018.
(Continued)

*Primary Examiner* — Vu Le
*Assistant Examiner* — Courtney Joan Nelson
(74) *Attorney, Agent, or Firm* — Larry Liberchuk (57) ABSTRACT

The present invention relates to X-ray image data analysis of a part of a cardiovascular system of a patient in order to estimate a level of inflammation in the part of the cardiovascular system. X-ray image data is received, a segmented model of the part of the cardiovascular system is generated and predetermined features related to inflammation are extracted from the segmented model. The extracted features are used as input to an inflammation function for calculating inflammation values of which each represents a level of inflammation in the part of the cardiovascular system. The image data analysis can improve the estimation of inflammation. Furthermore, the inflammation values can be presented to a user together with suggestions for performing actions. This can for example enable a prediction of plaque
(Continued)

development as well as future acute coronary syndrome events.

12 Claims, 4 Drawing Sheets

(51) Int. Cl.
*A61B 6/00* (2006.01)
*G06T 15/08* (2011.01)

(52) U.S. Cl.
CPC .... *G06T 15/08* (2013.01); *G06T 2207/30048* (2013.01); *G06T 2211/40* (2013.01)

(56) References Cited

U.S. PATENT DOCUMENTS

| | | | |
|---|---|---|---|
| 2010/0156898 A1 | 6/2010 | Voros | |
| 2010/0278405 A1 | 11/2010 | Kakadiaris | |
| 2015/0016702 A1 | 1/2015 | Huizenga | |
| 2015/0112182 A1* | 4/2015 | Sharma | A61B 5/7264 600/408 |
| 2020/0034968 A1 | 1/2020 | Freiman | |

FOREIGN PATENT DOCUMENTS

| | | | |
|---|---|---|---|
| WO | WO-2007017263 A2 * | 2/2007 | ............. A61B 5/444 |
| WO | WO2011069120 A1 | 6/2011 | |
| WO | WO2011123772 A2 | 10/2011 | |
| WO | WO-2012142455 A2 * | 10/2012 | ............... A61B 8/06 |
| WO | WO-2016024128 A1 * | 2/2016 | ............. G16H 50/30 |
| WO | WO2016024128 A1 | 2/2016 | |

OTHER PUBLICATIONS

Freiman M. et al., "Improving CCTA-Based Lesions' Hemodynamic Significance Assessment by Accounting for Partial Volume Modeling in Automatic Coronary Lumen Segmentation", Medical Physics—Wiley Online Library, Medical Physics, Mar. 17, 2017 (Mar. 17, 2017), vol. 44, issue 3, pp. 1040-1049, XP055443247.
Nakanishi K. et al., "Augmented Inflammation in Pericoronary Adipose Tissue is Associated with Future Acute Coronary Syndrome in Patients with Coronary Artery Disease," European Heart Journal, vol. 34, No. suppl_1, p. 154, Aug. 2013.
Murray C. J. L. et al., "Global, Regional, and National Age-Sex Specific All-Cause and Cause-Specific Mortality for 240 Causes of Death, 1990-2013: A Systematic Analysis for the Global Burden of Disease Study 2013," Lancet, vol. 385, No. 9963, pp. 117-171, Jan. 10, 2015.
Pizzi C. et al., "Nonobstructive Versus Obstructive Coronary Artery Disease in Acute Coronary Syndrome: A Meta-Analysis", Journal of the American Heart Association, vol. 5, No. 12, pp. 1-14, Dec. 2016.
Kumar A. et al., "Acute Coronary Syndromes: Diagnosis and Management, Part I.," Symposium On Cardiovascular Diseases, Mayo Clinic Proceedings, vol. 84, No. 10, pp. 917-938, 2009.
Scot-Heart T. et al., "CT Coronary Angiography in Patients with Suspected Angina Due to Coronary Heart Disease (SCOT-HEART): An Open-Label, Parallel-Group, Multicentre Trial," Lancet, vol. 385, No. 9985, pp. 2383-2391, Jun. 13, 2015.
Meijbom W. B. et al., "Comprehensive Assessment of Coronary Artery Stenoses. Computed Tomography Coronary Angiography Versus Conventional Coronary Angiography and Correlation With Fractional Flow Reserve in Patients With Stable Angina," Journal of American College of Cardiology, vol. 52, No. 8, pp. 636-643, Nov. 8, 2008.
Coenen A. et al., "Fractional Flow Reserve Computed from Non-invasive CT Angiography Data: Diagnostic Performance of an On-Site Clinician-Operated Computational Fluid Dynamics Algorithm.," Radiology, vol. 274, No. 3, pp. 674-683, Mar. 2015.
Nørgaard B. L. et al., "Diagnostic Performance of Non-Invasive Fractional Flow Reserve Derived from Coronary CT Angiography in Suspected Coronary Artery Disease: The NXT Trial.," Journal of American College of Cardiology, vol. 63, No. 12, pp. 1145-1155, 2014.
Maurovich-Horvat P. et al., "Comprehensive Plaque Assessment by Coronary CT Angiography," Nature Reviews, Cardiology, vol. 11, No. 7, pp. 390-402, Apr. 2014.
Motoyama S. et al., "Plaque Characterization by Coronary Computed Tomography Angiography and the Likelihood of Acute Coronary Events in Mid-Term Follow-Up," Journal of American College of Cardiology, vol. 66, No. 4, pp. 337-346, 2015.
Puchner S. B. et al., "High-Risk Plaque Detected on Coronary CT Angiography Predicts Acute Coronary Syndromes Independent of Significant Stenosis in Acute Chest Pain: Results from the ROMICAT-II Trial," Journal of American College of Cardiology, vol. 64, No. 7, pp. 684-692, 2014.
Otsuka K. et al., "Napkin-Ring Sign on Coronary CT Angiography for the Prediction of Acute Coronary Syndrome," JACC Cardiovasc Imaging, vol. 6, No. 4, pp. 448-457, 2013.
Choi G. et al., "Coronary Artery Axial Plaque Stress and its Relationship with Lesion Geometry Application of Computational Fluid Dynamics to Coronary CT Angiography," JACC Cardiovasc. Imaging, vol. 8, No. 10, pp. 1156-1166, 2015.
Verhagen S. N. et al., "Perivascular Adipose Tissue as a Cause of Atherosclerosis," Atherosclerosis, vol. 214, No. 1. pp. 3-10, 2011.
Maurovich-Horvat P. et al., "Influence of Pericoronary Adipose Tissue on Local Coronary Atherosclerosis as Assessed by a Novel MDCT Volumetric Method," Atherosclerosis, vol. 219, No. 1, pp. 151-157, 2011.
Uchida Y. et al., "Human Pericoronary Adipose Tissue as Storage and Possible Supply Site for Oxidized Low-Density Lipoprotein and High-Density Lipoprotein in Coronary Artery," Journal of Cardiology, vol. 69, pp. 236-244, 2016.
Gorter P. M. et al., "Relation of Epicardial and Pericoronary Fat to Coronary Atherosclerosis and Coronary Artery Calcium in Patients Undergoing Coronary Angiography.," American Journal of Cardiology., vol. 102, No. 4, pp. 380-385, 2008.
Owen M. K. et al., "Perivascular Adipose Tissue and Coronary Vascular Disease," Arteriosclerosis, Thrombosis, and Vascular Biology,, vol. 34, No. 8, pp. 1643-1649, 2014.
Oikonomou E. et al., "Inflammation Quantification for Cardiovascular Disease Risk Characterisation." Oxford Technology Showcase 2016.
Wachira, J.K. et al., "Cardiovascular Disease and Bridging the Diagnostic Gap.," South Dakota Journal of Medicine., vol. 66, No. 9, pp. 366-369, Sep. 2013.

* cited by examiner

INFLAMMATION ESTIMATION FROM X-RAY IMAGE DATA

FIELD OF THE INVENTION

The present invention relates to an image data analysis device, an image data analysis system, a method for analyzing image data, and a computer program. In particular the invention relates to an image data analysis device for analyzing image data of a part of a cardiovascular system of a patient in order to estimate a level of inflammation in the part of the cardiovascular system. Image data can be provided from image scanners, in particular from X-ray tomography scanners, (e.g. computed tomography (CT) scanners, such as spectral CT scanners, cone-beam CT scanners, tomosynthesis scanners, digital X-ray systems, or the like).

BACKGROUND OF THE INVENTION

Coronary artery disease (CAD) is the most common cause for death globally. Among CAD patients, acute coronary syndrome (ACS) may develop from the erosion or rupture of obstructive or non-obstructive coronary atherosclerotic plaques. Coronary computed tomography angiography (CCTA) is a non-invasive technique to rule out CAD due to its high negative predictive value. CCTA is commonly used to characterize the anatomical appearance of existing coronary lesions. CCTA typically uses iodine-rich contrast material and CT scanning to examine arteries that supply blood to the heart and to determine whether they have been narrowed by plaque buildup.

Pericoronary adipose tissue volume was suggested to be correlated with the presence of plaque. It was furthermore suggested that the quality of the pericoronary adipose tissue measured by Hounsfield units (HU) may serve as an indicator for the presence of early inflammation. Inflammation in the pericoronary adipose tissue was associated with future ACS in patients with CAD. Pericoronary adipose tissue inflammation is characterized in CCTA by thresholding the CCTA data using a specific range of Hounsfield units (HU).

WO 2016/024128 shows a method for volumetric characterization of perivascular tissue using data gathered from a CT scan along a length of a blood vessel. The perivascular tissue is volumetrically characterized by quantifying radiodensity in each of one or more concentric layers of the perivascular tissue and determining whether one or more of the quantified radiodensity values are above or below a baseline radiodensity value. The radiodensity can in particular be quantified in HU.

SUMMARY OF THE INVENTION

It can be seen as an object of the present invention to provide an image data analysis device, an image data analysis system, a method for analyzing image data, and a computer program which allow improving an estimation of inflammation in a part of a cardiovascular system.

In a first aspect of the present invention an image data analysis device for analyzing X-ray image data of a part of a cardiovascular system of a patient in order to estimate a level of inflammation in the part of the cardiovascular system is presented. The image data analysis device comprises a data receiving unit, a data modeling unit, a feature extraction unit, and a data processing unit. The data receiving unit is configured for receiving X-ray image data comprising the part of the cardiovascular system of the patient. The data modeling unit is configured for generating a segmented model of the part of the cardiovascular system from the image data. The feature extraction unit is configured for extracting predetermined features related to inflammation from the segmented model. The data processing unit is configured for calculating inflammation values of an inflammation function depending on the extracted features. Each of the inflammation values represents a level of inflammation in the part of the cardiovascular system.

Since the image data analysis device comprises the feature extraction unit for extracting predetermined features related to inflammation from the segmented model, predetermined features can be provided as input to the inflammation function. This allows improving the estimation of a level of inflammation in the part of the cardiovascular system as the estimation of the inflammation is in contrast to devices relying solely on HU values less influenced by imaging artifacts such as beam-hardening and motion effects among others. Non-invasive assessment of vulnerable plaque, (i.e., plaque with a high probability to rupture, and prediction of future ACS is enabled by the image data analysis device). In particular assessment of vulnerable plaque and prediction of probability of ACS for patients undergoing CCTA due to suspected CAD can be enabled. Furthermore, an improved assessment of CAD in an early stage before any physical damage occurred can be enabled that allows for improving a treatment plan for the patient and/or a treatment by medication.

The X-ray image data is image data acquired with X-ray tomography scanners, (e.g. computed tomography (CT) scanners, such as spectral CT scanners, cone-beam CT scanners, tomosynthesis scanners, digital X-ray systems, or the like).

The part of the cardiovascular system can for example be carotid arteries, cardiac anatomy, coronary tree or a part of the coronary tree of the patient. In this case the data modeling unit can for example be configured for generating the segmented model in form of an anatomical model, (e.g., a three dimensional anatomic model, of the coronary tree of the patient from the image data).

The segmented model comprises segments such as vessel walls, tissues, lumina, or liquids of the part of the cardiovascular system. The segments can for example be coronary tree vessel walls, pericoronary adipose tissue, bones, coronary lumen, blood, or other segments. The materials of the segments have different elements, density and/or thickness that allows to differentiate between the segments. The data modeling unit can be configured to generate the segmentation model based on algorithms such as the one presented in M. Freiman, H. Nickisch, S. Prevrhal, H. Schmitt, M. Vembar, P. Maurovich-Horvat, P. Donnelly, and L. Goshen, "Improving CCTA-based lesions' hemodynamic significance assessment by accounting for partial volume modeling in automatic coronary lumen segmentation", Med. Phys. Vol. 44, no. 3, pp. 1040-1049, March 2017, which is incorporated herein by reference. Additionally, the segments can be adjusted manually and/or in dependence of predetermined parameters.

The predetermined features can be designed manually and/or learned from the image data using a machine-learning method. Manually designed features include for example tissue volume, HU values, gradient-based features, and texture features. The texture features, such as a co-occurrence matrix or the like, can for example be calculated over maps of the other features. Machine-learning methods include for example dictionary learning, deep-learning or other machine-learning methods. All predetermined features can for example be included into a real-valued vector patient_specific_features∈R".

The data processing unit can be configured for using the vector patient_specific_features as input to the inflammation function in order to calculate inflammation values at each voxel of an image representing the part of the cardiovascular system, only at voxels from which features were extracted from the segmented model, or only at voxels of one or more segments of the segmented model.

In one embodiment of the image data analysis device the feature extraction unit is configured to extract predetermined features based on pattern-recognition performed on the segmented model. The pattern-recognition can be performed by a pattern-recognition algorithm. The pattern-recognition algorithm can for example be a rule-based algorithm, a machine-learned algorithm or any other suitable algorithm.

The inflammation function can be optimized by machine learning methods, (e.g., supervised-learning methods, such as deep neural networks, regression forests, random forests, support vector machines, or other machine learning methods). In supervised-learning methods multiple pairs of input and output data, known as training data are used to find the inflammation function based on optimization criteria. The training data comprises actual levels of inflammation that can be used to compare the error between the inflammation values estimated by the inflammation function and the actual values of inflammation in the training data. The training procedure can be described by $$\hat{f} = \underset{f}{\mathrm{argmin}}\, \mathrm{Error}(f(\text{patient\_specific\_pericoronary\_features}), x)$$

in which $\hat{f}$ is the optimized inflammation function, $f$ is the current inflammation function which is to be optimized, Error is the machine-learning model used for the optimization and x is the actual value of inflammation in the training data. The machine-learning model can comprise one or more regularization terms. Overfitting can for example be avoided using standard techniques such as cross-validation, (e.g., leave-one-out-cross validation, or the like). The optimization can be performed using standard techniques, (e.g., stochastic gradient decent algorithms among others).

The inflammation function can be optimized in dependence of training data comprising histology analysis data, disease outcome data, and/or data received from medical imaging techniques allowing to estimate a level of inflammation. Hence training data can comprise histology analysis data, disease outcome data, data received from medical imaging techniques allowing to estimate a level of inflammation, or any combination thereof. Histology data comprises information about the level of inflammation derived from microscopic study of the part of the cardiovascular system. Disease outcome data comprises information about the occurrence of the disease, the time between acquiring the image data and the occurrence of the disease, level of the disease, or any other information regarding the outcome of the disease. Disease outcome data can also comprise information of two or more diseases. A disease can for example be an ACS. In this case the disease outcome data is ACS outcome data and the ACS outcome data comprises information about occurrence of ACS, level of ACS, time between a CCTA and ACS event, or any other information regarding the ACS outcome. Data received from medical imaging techniques allowing to estimate a level of inflammation can for example be PET data or any other data that allows estimating the level of inflammation.

The image data analysis device can comprise a visualization unit. The visualization unit can be configured for visualizing the inflammation values or the inflammation values together with the segmented model. Therefore, the visualization unit can be configured to generate a map of inflammation values for each voxel of the image representing the part of the cardiovascular system, only for voxels from which features were extracted from the segmented model or only for voxels of one or more segments of the segmented model. The resulting map quantifies inflammation and allows for visually and quantitatively assessing a risk of plaque to be vulnerable and a risk for development of new vulnerable plaque. The visualization unit can be configured to generate different views based on the inflammation values. Views can include a multi-planar reformatted vessel tree view, a three dimensional color-coded surface mesh view, a flattened surface representation or any other view that allows for deriving information about inflammation and risk of plaque vulnerability and risk for development of new vulnerable plaque. In the multi-planar reformatted vessel tree view the map can for an example of a cardiac anatomy be sampled along the coronary tree centerlines using straight multi-planar or curved multi-planar reformation to generate a view of the inflammation value map along the coronaries. The visualization unit can be configured to allow zooming in and out of a view, such that for example one vessel can be viewed or the entire coronary tree. In the three dimensional color-coded surface mesh view the part of the cardiovascular system can be overlayed with a surface mesh which is color-coded with inflammation values. In the flattened surface representation, the inflammation values can be color-coded with inflammation values on a flattened mesh.

The image data can for example comprise a CT image of the part of the cardiovascular system reconstructed from CT projection data acquired by a CT scanner.

The image data can be spectral image data, such as spectral CT data. Spectral image data is image data that comprises image data at at least two different levels of energy. Spectral CT data is CT data that comprises CT data at at least two different levels of energy. The spectral CT data can for example be acquired with a spectral CT scanner, such as a photon-counting CT scanner, a dual source CT scanner, a CT scanner performing kVp switching, or a CT scanner with a multilayer detector such as a dual-layer detector system that separates X-ray flux at the detector into two levels of energy. The dual source CT scanner can for example comprise two X-ray sources operated at different energies at different locations and two detector arrays each receiving an X-ray flux provided by one of the X-ray sources. The CT scanner performing kVp switching can for example comprise one X-ray source which is rapidly switched between two different voltages. The CT scanner with the multilayer detector can for example have one or more different filters such as a tin or gold foil between detector layers.

In case that the image data is spectral image data, such as spectral CT data, the data modeling unit can be configured to use spectrally enabled algorithms incorporating the spectral image data. This can allow for improved segmentation of the segmented model. Additionally or alternatively the feature extraction unit can be configured to extract spectrally dependent features, such as spectrally corrected HU values, (i.e., monochromatic HU values) and/or spectral results such as spectral fat maps, Z-effective values, or other information that can be derived from spectral image data and in particular from spectral CT data. Spectral fat maps can be obtained based on material decomposition using spectral CT data. The spectral CT data can for example be decomposed in the projection domain or the image domain using a two-material basis. A two-material basis can for example be iodine and water or photo-electric effect and Compton scattering effect. Furthermore, texture features such as co-occurrence matrix or the like calculated over maps describing the features of HU values, spectral corrected HU values, spectral results, and gradient based features can be designed features that the feature extraction unit can be configured to extract. The predetermined features can be included in the real-valued vector patient_specific_features.

The image data can alternatively be polychromatic CT data. The polychromatic CT data can for example be acquired by a CT scanner with an energy integrating detector.

The data receiving unit can furthermore be configured for receiving additional patient data, (e.g. demographic data, disease outcome data, lab examination result data, or any other data relevant for estimating inflammation). Demographic data can comprise sex, age, weight, height of the patient, or the like. Lab examination result data can for example comprise histology data or any other data obtained by lab examination.

The data processing unit can be configured to estimate a probability for development of plaque in the part of the cardiovascular system, a probability for rupturing of plaque in the part of the cardiovascular system, or a probability for development of plaque in the part of the cardiovascular system and a probability for rupturing of plaque in the part of the cardiovascular system based on the inflammation values. This allows for predicting a probability of a future ACS event. The data processing unit can therefore be configured for calculating probability values of a probability function for rupturing of plaque depending on inflammation values and/or a probability function for development of plaque depending on inflammation values. The respective probability functions can be optimized by machine learning methods based on training data.

The image data analysis device can comprise a user interface. The user interface can be configured to provide an interaction between a user and the image data analysis device. The user can estimate a level of inflammation in the part of the cardiovascular system based on statistical descriptors of the inflammation value distribution, including statistical descriptors such as mean, standard deviation, median, maximal value, minimal value, histogram-based features, or any other statistical descriptor. Furthermore for example for cardiac anatomy, quantities such as total inflammation burden, percentage inflammation burden out of entire pericoronary adipose tissue, mean inflammation value over the coronary tree or a group of lesions in the coronary tree, or the like can be used for estimating a level of inflammation over the entire coronary tree. The user interface can also allow the user to select one or more areas in the map, (e.g. a specific lesion), visualized by the visualization unit in order to perform an action on the data included in the selected area. In particular, the user can estimate inflammation of the selected area based on statistical descriptors. This allows to support a decision how to treat a patient. The user interface can furthermore be configured to provide suggestions for actions, such as a treatment of the patient in dependence of the inflammation values. Comparison of level of inflammation over time can allow to assess disease progression or response to a therapy. Therefore, the inflammation values can support a decision to treat a patient by medication or an alternative medical intervention, (e.g. a surgery).

In a further aspect of the present invention an image data analysis system is presented. The system comprises an image data analysis device according to any embodiment of the present invention and an image scanner for generating X-ray image data of a part of a cardiovascular system of a patient. The image data analysis system is configured to provide the X-ray image data generated by the image scanner to the image data analysis device for analyzing the image data.

The image scanner is in particular an X-ray tomography scanner, (e.g. a CT scanner, such as a spectral CT scanner, a cone-beam CT scanner, a tomosynthesis scanner, a digital X-ray system, or the like). In case that the image scanner is a CT scanner, it can be configured for generating image data for CCTA.

The image data analysis system can comprise a training device for optimizing the inflammation function of the image data analysis device. The training device can be configured to train the inflammation function using machine learning methods, (e.g., supervised-learning methods, such as deep neural networks, regression forests, random forests, support vector machines, or other machine learning methods). Additionally, or alternatively, the training device can be configured to optimize the inflammation function in dependence of training data. The training data can comprise histology analysis data, disease outcome data, and/or data received from medical imaging techniques. Hence the training device can for example be configured for receiving image data together with associated histology data and disease data and for training the inflammation function based on the training data in order to optimize the inflammation function.

The image data analysis system can be configured for analyzing the part of the cardiovascular system of the patient. The image data analysis system can furthermore be configured to estimate a level of inflammation, (e.g., a level of pericoronary inflammation in case that the part of the cardiovascular system analyzed is a cardiac anatomy). In a further aspect of the present invention a method for analyzing X-ray image data of a part of a cardiovascular system of a patient in order to estimate a level of inflammation in the part of the cardiovascular system is presented. The method comprises the steps:

receiving X-ray image data comprising the part of the cardiovascular system of the patient, generating a segmented model of the part of the cardiovascular system from the image data, extracting predetermined features related to inflammation from the segmented model, calculating inflammation values of an inflammation function depending on the extracted features. Each of the inflammation values represents a level of inflammation in the part of the cardiovascular system.

Extracting predetermined features can be performed by performing pattern-recognition on the segmented model.

The image data can for example be received from CCTA. The image data can for example be spectral CT data. The inflammation function can be optimized by machine learning methods.

The method can comprise a step of visualizing the inflammation values or the inflammation values together with the segmented model. Visualizing can be performed by generating different views based on the inflammation values.

In a further aspect of the present invention a computer program for analyzing X-ray image data of a part of a cardiovascular system of a patient in order to estimate a level of inflammation in the part of the cardiovascular system is presented. The computer program comprises program code means for causing a processor to carry out the method as defined in claim 12, when the computer program is run on the processor.

In other embodiments the computer program can comprise program code means for causing a processor to carry out a method according to any embodiment of the method of the invention.

In a further aspect of the present invention a use of the image data analysis device according to any embodiment of the present invention for predicting ACS is presented.

The image data analysis device can also be used for estimating a probability for development of plaque in the part of the cardiovascular system and/or a probability for rupturing of plaque in the part of the cardiovascular system.

In a further aspect of the present invention a use of the method according to any embodiment of the present invention for predicting ACS is presented.

The method can also be used for estimating a probability for development of plaque in the part of the cardiovascular system and/or a probability for rupturing of plaque in the part of the cardiovascular system.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
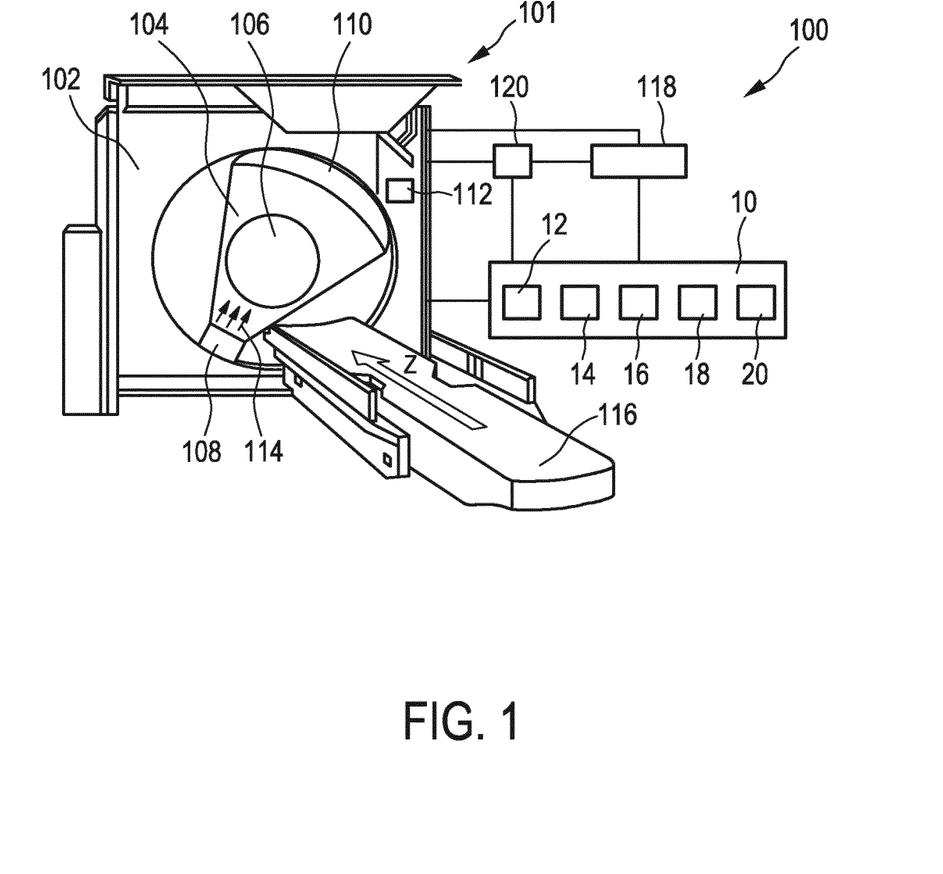
FIG. 1 shows schematically and exemplarily an embodiment of an image data analysis system comprising a first embodiment of an image data analysis device.

FIG. 1 shows schematically and exemplarily an embodiment of the image data analysis system 100 including an embodiment of the image data analysis device 10. This embodiment of the image data analysis system 100 comprises a CT scanner 101. In other embodiments the image data analysis system 100 can for example comprise any other kind of X-ray tomography scanner, (e.g. a spectral CT scanner, a cone-beam CT scanner, a tomosynthesis scanner, a digital X-ray system, or the like).

The image data analysis system 100 additionally to the image data analysis device 10 and CT scanner 101 comprises a user interface 118 and a training device 120.

The CT scanner 101 comprises a stationary gantry 102, a rotatable gantry 104, an examination region 106, a radiation source 108, a radiation sensitive detector array 110, an image data processing device 112, and a subject support 116.

The rotatable gantry 104 is rotatably supported by the stationary gantry 102 in order to rotate around a z-axis of the examination region 106.

The radiation source 108 in this embodiment is an x-ray tube. In other embodiments more than one radiation source can be part of the image scanner. The radiation source 108 and the radiation sensitive detector array 110 are rotatably supported by the rotatable gantry 104 and arranged around the examination region 106. In other embodiments more than one detector array can be part of the image scanner, (e.g., two detectors in two layers).

In order to perform a scan of a subject, the subject is arranged on the subject support 116 and moved into the examination region 106. The subject support 116 is movable along the z-axis in order to move the subject into the examination region 106.

The radiation source 108 emits radiation 114 that travels from the radiation source 108 through the examination region 106 and the subject (not shown) to the radiation sensitive detector array 110. The radiation sensitive detector array 110 hence receives data representing the image in form of a projection of one angle setting. In order to reconstruct an image from the data representing the image it is necessary to receive projections from several angles. Therefore, the radiation source 108 and the radiation sensitive detector array 110 are rotated around the examination region 106 to scan the subject. During the scan the radiation source 108 emits radiation 114 with several angles and the radiation sensitive detector array 110 receives that radiation 114 under several angles. The scanned angular range can for example be 180°, 270° or 360°. In another embodiment the detector array 110 can receive radiation with at least two different energy levels.

The radiation sensitive detector array 110 provides the data representing the image to the image data processing device 112. The image data processing device 112 reconstructs the image from the data representing the image in order to generate X-ray image data. The CT scanner 101 in this embodiment scans a part of a cardiovascular system of a patient. The X-ray image data therefore comprises a part of a cardiovascular system of a patient. The X-ray image data generated by the CT scanner 101 is provided to the image data analysis device 10 for analyzing the image data.

Although in the above described embodiment the image data analysis system 100 is adapted to analyze images of a subject, it can also be adapted to analyze images of an object, (e.g. a part of an artificial cardiovascular system). Therefore, in particular the subject support 116 can be adapted for supporting objects (not shown).

The user interface 118 in this embodiment is a touch display. The user interface 118 is optional and can be any other interface that enables an interaction between a user and the image data analysis system 100, for example a personal computer or a screen, a keyboard and a mouse. The user interface 118 receives data from the user using the image data analysis system 100, for example parameters such as a rotation angle or a range of angles to be scanned, kV settings for the scan, or other parameters. The user interface 118 can also be used to control the image data analysis system 100, the image data analysis device 10, and the training device 120.

The user interface 118 furthermore provides images provided by the image data analysis system 100 to the user using the user interface 118.

In this embodiment of the image data analysis system 100 the components of the system, (i.e., the CT scanner 101, the image data analysis device 10, the training device 120, and the user interface 118) are connected by wire. Alternatively, the components can also be wirelessly connected (not shown).

The image data analysis device 10 comprises a data receiving unit 12, a data modeling unit 14, a feature extraction unit 16, a data processing unit 18, and a visualization unit 20. The image data analysis device 10 is used for analyzing X-ray image data of the part of the cardiovascular system of the patient in order to estimate a level of inflammation in the part of the cardiovascular system. This allows for predicting whether plaque present in the part of the cardiovascular system is likely to rupture and therefore to cause an ACS, as well as predicting whether development of new plaque in the part of the cardiovascular system is likely.

The data receiving unit 12 receives X-ray image data comprising the part of the cardiovascular system of the patient from the CT scanner 101. In this embodiment the CT scanner 101 is used for scanning the cardiac anatomy of a patient. Therefore, X-ray image data comprising the cardiac anatomy is received at the data receiving unit 12. The image data is reconstructed from CT projection data acquired with the CT scanner 101. In other embodiments spectral CT data can be acquired, for example using a dual-layer detector system that separates X-ray flux at the detector into two levels of energy. Alternatively, any other system for deriving spectral CT data can be used, for example using another type of multilayer detector, a photon-counting CT scanner, a dual source CT scanner, or a CT scanner performing kVp switching. The data receiving unit 12 furthermore receives additional patient data in the form of demographic data, disease outcome data, and lab examination result data. Any other data relevant for estimating inflammation can also be provided as additional patient data. The additional patient data, however, is not essential for estimating inflammation.

The data modeling unit 14 generates a three dimensional anatomical model of the coronary tree from the image data based on the algorithm proposed in M. Freiman, H. Nickisch, S. Prevrhal, H. Schmitt, M. Vembar, P. Maurovich-Horvat, P. Donnelly, and L. Goshen, "Improving CCTA-based lesions' hemodynamic significance assessment by accounting for partial volume modeling in automatic coronary lumen segmentation", Med. Phys. Vol. 44, no. 3, pp. 1040-1049, March 2017. The anatomical model is segmented in segments such as coronary tree vessel walls, pericoronary adipose tissue, coronary lumen, and other segments of the cardiac anatomy of the patient. Additionally the segments can be adjusted manually using various tools known to the skilled person, (e.g. commercially available tools such as Philips IntelliSpace Portal with Comprehensive Cardiac Application (CCA)). In other embodiments other suitable algorithms or methods for segmenting the cardiac anatomy can be used. Furthermore, a segmented model of any other part of the cardiovascular system can be generated if that part is scanned and image data of the scanned part of the cardiovascular system is received by the data receiving unit 12.

The feature extraction unit 16 extracts predetermined features related to inflammation from the segmented model generated by the data modeling unit 14. In this embodiment the predetermined features are related to pericoronary adipose tissue inflammation. Hence some of the predetermined features are manually designed and other predetermined features are learned by a machine learning algorithm. The predetermined features are extracted based on pattern-recognition algorithms using the feature extraction unit 16. Manually designed features include inter alia conventional HU values at and around the coronary adipose tissue, gradient-based features, and texture features of the other features, in particular a co-occurrence matrix calculated over maps of the other features. The machine-learning methods include dictionary learning and deep-learning methods. In other embodiments any other machine-learning method can be used for training the feature extraction unit 16 to extract predetermined features. All extracted predetermined features are included into a real-valued vector patient_specific_pericoronary_features$\in \mathbb{R}^n$.

The data processing unit 18 uses the vector patient_specific_pericoronary_features as input to an inflammation function $f$ in order to calculate inflammation values at each voxel representing pericoronary adipose tissue as determined by the segmentation performed by the data modeling unit 14, (i.e., the inflammation function $f$ depending on the extracted features ($f$ (patient_specific_pericoronary_features)=inflammation_values) is only calculated at voxels of segments that are determined to be pericoronary adipose tissue). Each of the inflammation values represents a level of inflammation. Hence the inflammation function $f$ can be used to estimate the level of inflammation at each voxel representing pericoronary adipose tissue. The inflammation function $f$ describes implicitly the statistical relation between the input extracted features and the output inflammation values representing level of inflammation. In other embodiments the data processing unit 18 can also calculate inflammation values at each voxel of an image representing the scanned part of the cardiovascular system, only at voxels from which features were extracted from the segmented model, or only at voxels of one or more segments of the segmented model.

Several machine-learning models can be used to find and optimize the inflammation function $f$. In this embodiment supervised-learning methodology is used. In this methodology, multiple pairs of inputs and outputs, known as training data are used to find the inflammation function $f$ using some optimization criteria. The inflammation function $f$ is generated once and can then be used for estimating inflammation values in the cardiac anatomy of various patients. In order to find and optimize the inflammation function in this embodiment the training device 120 is used based on deep neural networks. Other supervised-learning methods include regression forests, random forests, support vector machines and other supervised-learning methods. Furthermore training data comprising an actual level of inflammation required to train the inflammation function $f$ is obtained by histology analysis of pericoronary adipose tissue of patients that underwent CCTA exam in order to generate histology analysis data and studying occurrence of ACS and the time between CCTA exam and the ACS event in order to generate ACS outcome data. In other embodiments further training data can be obtained, (e.g., data received from medical imaging techniques that allow to estimate a level of inflammation, such as PET data).

The training procedure performed by the training device 120 in order to optimize the inflammation function can be described by:

$$\hat{f} = \underset{f}{\arg\min} \operatorname{Error}(f(\text{patient\_specific\_features}), x)$$

in which $\hat{f}$ is the optimized inflammation function, $f$ is the current inflammation function, Error is the machine-learning model used for the optimization and x is the actual value of inflammation in the training data. In other embodiments the machine-learning model comprises one or more regularization terms. Overfitting is avoided by leave-one-out-cross validation in this embodiment. Any other standard techniques such as any other cross-validation or the like can also be used in order to avoid overfitting. The optimization is performed by stochastic gradient decent algorithms in this embodiment. Any other standard technique can be used for the optimization.

In other embodiments the data processing unit 18 is configured to estimate a probability for development of plaque in the part of the cardiovascular system and/or a probability for rupturing of plaque in the part of the cardiovascular system based on the inflammation values. This allows for predicting a probability of a future ACS event. The data processing unit therefore calculates probability values of a probability function for rupturing of plaque depending on inflammation values or a probability function for development of plaque depending on inflammation values. The respective probability functions can be optimized by machine learning methods based on training data.

The visualization unit 20 visualizes the inflammation values or inflammation values together with the anatomical model of the coronary tree. The visualization unit 20 in this embodiment is optional and images can be provided as output via the user interface 118. The visualization unit 20 generates a map of inflammation values for each voxel of pericoronary adipose tissue as determined by the segmentation performed by the data modeling unit 14. In other embodiments the visualization unit 20 can also generate a map of inflammation values for each voxel of an image representing the scanned part of the cardiovascular system, only for voxels from which features were extracted from the segmented model, or only for voxels of one or more segments of the segmented model. The resulting map quantifies pericoronary adipose tissue inflammation and allows for visually and quantitatively assessing a risk of plaque to be vulnerable and a risk for development of new vulnerable plaque.

The visualization unit 20 can generate different views (an example view 300 can be found in FIG. 4) based on the inflammation values. This allows to provide more information to the user. Views include a multi-planar reformatted vessel tree view (cf. FIG. 4), a three dimensional color-coded surface mesh view, a flattened surface representation or any other view that allows for deriving information about inflammation and risk of plaque vulnerability and risk for development of new vulnerable plaque. In the multi-planar reformatted vessel tree view the map is sampled along the coronary tree centerlines using straight multi-planar or curved multi-planar reformation to generate a view of the inflammation value map along the coronaries. The visualization unit 20 in this embodiment allows zooming in and out of the view, such that for example one vessel can be viewed or the entire coronary tree.

In the three dimensional color-coded surface mesh view the part of the cardiovascular system can be overlayed with a surface mesh which is color-coded with inflammation values.

In the flattened surface representation, the inflammation values can be color-coded with inflammation values on a flattened mesh.

In this embodiment the image data analysis device 10 furthermore comprises a computer program for analyzing image data of a part of a cardiovascular system of a patient in order to estimate a level of inflammation in the part of the cardiovascular system. The computer program is stored in a memory (not shown). The computer program comprises program code means for causing the image data analysis device 10 to carry out the respective method as described for FIG. 3, when the computer program is run on the image data analysis device 10. Alternatively, or additionally, other computer programs can be included in the memory, (e.g., for performing image processing tasks, (e.g. anti-aliasing, artifact reduction, or image manipulation, such as drawing, measuring distances, or the like)).

Figure 2:
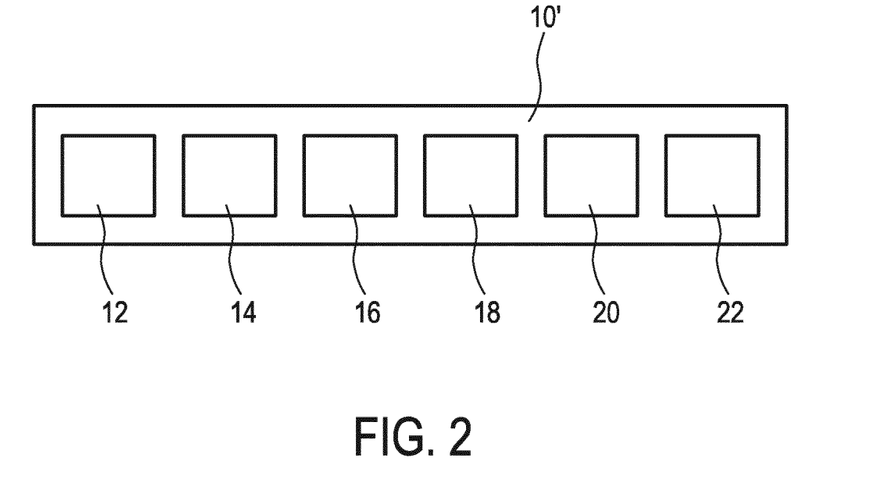
FIG. 2 shows schematically and exemplarily a second embodiment of an image data analysis device.

FIG. 2 shows schematically and exemplarily a second embodiment of an image data analysis device 10'. The second embodiment of the image data analysis device 10' is similar to the first embodiment of the image data analysis device 10. However, the second embodiment of the image data analysis device 10' comprises a user interface 22 and uses spectral CT data for analyzing a part of a cardiovascular system of a patient. In this embodiment the cardiac anatomy of the patient is analyzed. Any other part of the cardiovascular system can alternatively be analyzed.

The image data analysis device 10' comprises a data receiving unit 12, a data modeling unit 14, a feature extraction unit 16, a data processing unit 18, a visualization unit 20, and a user interface 22.

The data receiving unit 12 in this embodiment receives spectral CT data. The spectral CT data can be received wirelessly or via a wired connection. The spectral CT data is acquired by a spectral CT scanner, which in this embodiment is a dual-layer system that separates the X-ray flux at the detector into two levels of energy. Therefore, the spectral CT data in this embodiment comprises CT data acquired at two different levels of energy. Alternatively, other spectral CT scanners can be used that allow acquiring CT data with two or more than two different levels of energy.

The data modeling unit 14 generates a segmented model in the form of a three dimensional anatomical model of the coronary tree based on the spectral CT data which allows for an enhanced segmentation. The use of spectral CT data allows an easier differentiation between different materials, such that the segmentation can be enhanced.

The feature extraction unit 16 extracts predetermined features from the segmented model. As spectral CT data is used, additional predetermined features can be designed. In this embodiment manually designed features include conventional HU values at and around the coronary adipose tissue, spectrally corrected HU values, (i.e., monochromatic HU values), at and around the coronary adipose tissue, spectral results such as spectral fat maps, Z-effective values among others at and around the coronary adipose tissue, gradient-based features, and texture features. The texture features in this embodiment are co-occurrence matrices calculated over maps of the aforementioned features. The predetermined features are then included into a real-valued vector patient_specific_pericoronary_features$\in R^n$.

The data processing unit 18 uses vector patient_specific_pericoronary_features as input to an inflammation function, which is generated in the manner as described for the first embodiment of the image data analysis device 10. The data processing unit 18 in the second embodiment of the image data analysis device 10' furthermore estimates a probability for development of plaque in the part of the cardiovascular system and/or a probability for rupturing of plaque in the part of the cardiovascular system based on the inflammation values. Therefore, the data processing unit 18 uses probability functions for each of the two probabilities. The probability functions can be generated in a manner as described for the first embodiment of the image data analysis device 10.

The visualization unit 20 visualizes the inflammation values in a manner as described for the first embodiment of the image data analysis device 10.

The user interface 22 allows an interaction between a user and the image data analysis device 10'. In this embodiment the user interface 22 is a clinical decision support unit. The user interface 22 therefore provides suggestions for actions such as a treatment of the patient in dependence of the inflammation values. In this embodiment the user can estimate a level of inflammation in the part of the cardiovascular system the user is interested in based on statistical descriptors of the inflammation value distribution, including statistical descriptors such as mean, standard deviation, median, maximal value, minimal value, histogram-based features, or any other statistical descriptor. The user can for example select to estimate a level of inflammation at a specific lesion, an entire vessel or the entire coronary tree. The user interface 22 allows a user to estimate a level of inflammation over the entire coronary tree using quantities such as total inflammation burden, percentage inflammation burden out of entire pericoronary adipose tissue, mean inflammation value over the coronary tree or a group of lesions in the coronary tree, or the like. The user interface 22 in this embodiment allows the user to select one or more areas in the map, (e.g. a specific lesion), visualized by the visualization unit 20 in order to perform an action on the data included in the selected area. In particular, the user can estimate inflammation of the selected area based on statistical descriptors. This allows to support a decision how to treat a patient. Comparison of the level of inflammation over time can allow to assess disease progression or response to a therapy. Therefore, the inflammation values can support a decision to treat a patient by medication or an alternative medical intervention, (e.g. a surgery).

The user interface 22 in this embodiment furthermore provides the probability for development of plaque in a selected area of the cardiovascular system and/or a probability for rupturing of plaque in a selected area of the cardiovascular system based on the inflammation values. The user interface 22 furthermore provides suggestions for further actions based on the probabilities. Providing suggestions by the user interface 22 is not an essential feature and in other embodiments the user interface can be limited to interacting with the user without providing suggestions. In yet another embodiment the user interface can be configured to provide suggestions automatically without user interaction and limit the user to select one of the suggested actions. The user interface can comprise an additional drug unit that is configured to provide a patient with a drug in dependence of the selected action or automatically in dependence of the estimated probability of rupturing of plaque or development of plaque.

Figure 3:
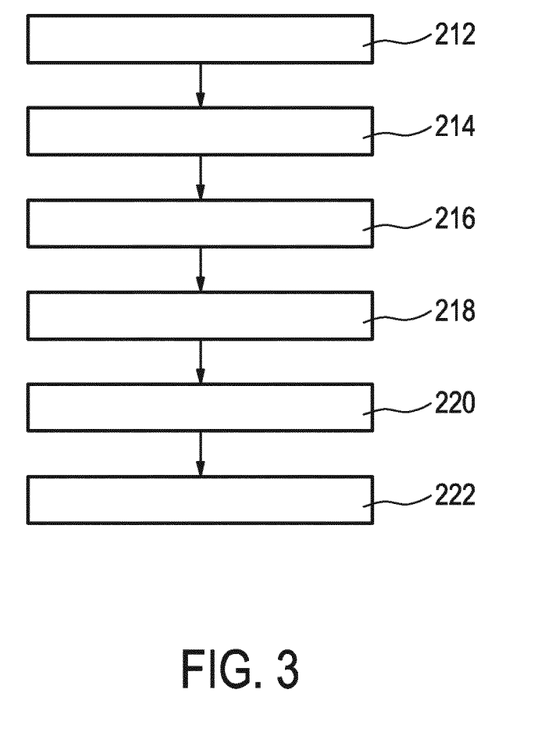
FIG. 3 shows schematically and exemplarily an embodiment of a method for analyzing image data.

FIG. 3 shows schematically and exemplarily an embodiment of a method for analyzing X-ray image data of a part of a cardiovascular system of a patient in order to estimate a level of inflammation in the part of the cardiovascular system. In step 212 X-ray image data comprising the part of the cardiovascular system of the patient is received. In step 214 a segmented model of the part of the cardiovascular system is generated from the image data. In step 216 predetermined features related to inflammation are extracted from the segmented model. In this embodiment the extraction of the predetermined features is performed by performing pattern-recognition on the segmented model. Inflammation values of an inflammation function depending on the extracted features are calculated in step 218. Each of the inflammation values represents a level of inflammation in the part of the cardiovascular system. In step 220 the inflammation values or the inflammation values together with the segmented model are visualized. Different views can be generated based on the inflammation values. In step 222 suggestions for actions in dependence of the inflammation values are provided. A user can perform an action based on the suggestions. Steps 220 and 222 are optional. The method can for example be performed on an image data analysis device 10 or 10' as described in FIG. 1 or 2.

Figure 4:
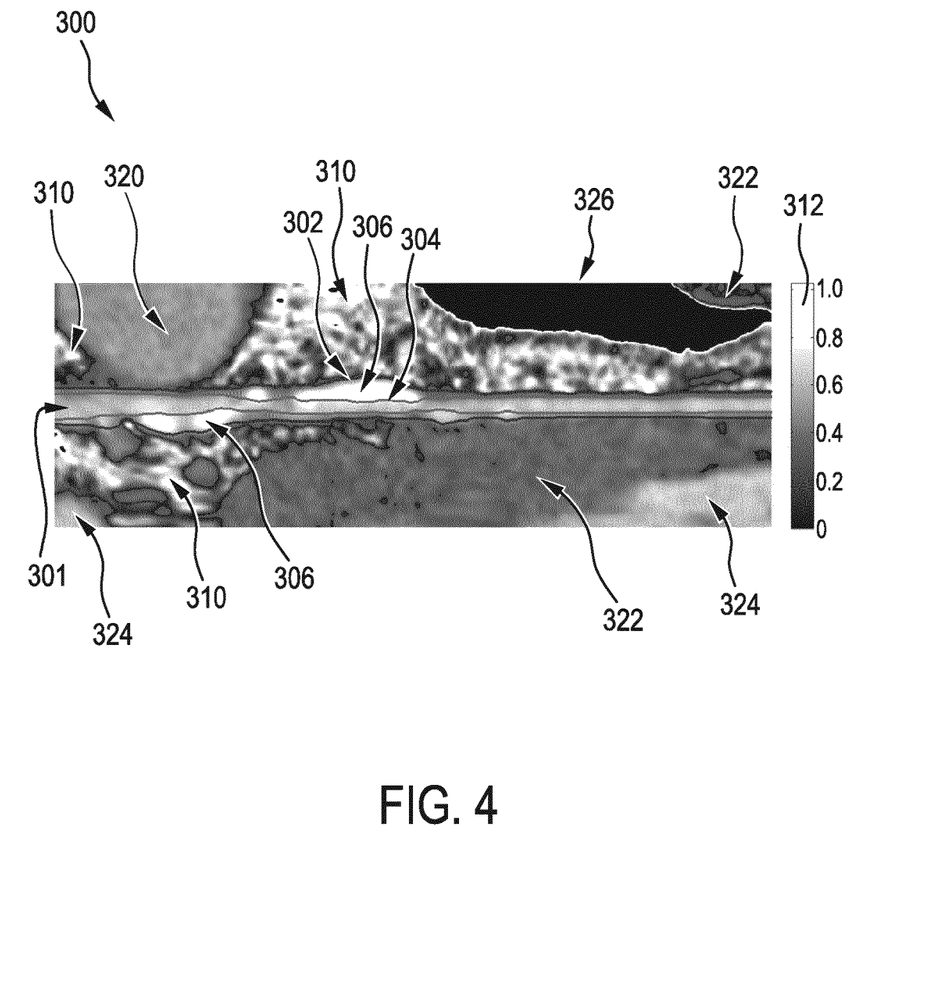
FIG. 4 shows a visualization of image data of a coronary artery analyzed with an image data analysis device in form of an exemplary view.

FIG. 4 shows a visualization of X-ray image data of a coronary artery in a first view 300 analyzed with an image data analysis device. The view 300 shows inflammation values as color-coded map overlaid over a straight multi-plannar reformatted view of a coronary artery 301 with several lesions. The coronary artery 301 has a coronary wall 302 and a narrowed lumen 304 due to plaque 306. The plaque 306 developed at lesions in the coronary artery 301. The coronary artery 301 is surrounded by high inflammation value regions 310 of pericoronary adipose tissue. The inflammation value scala 312 has higher values for brighter color. Higher levels of inflammation increase the probability of nearby plaque 306 to be vulnerable, (i.e., the plaque 306 surrounded by tissue with high level of inflammation is likely to rupture and to cause an ACS event in the future). The view 300 furthermore shows blood in left atrium 320, cardiac muscle 322, blood in left ventricle 324, and air 326.

While the invention has been illustrated and described in detail in the drawings and foregoing description, such illustration and description are to be considered illustrative or exemplary and not restrictive; the invention is not limited to the disclosed embodiments. For example, it is possible to operate the invention in an embodiment wherein the part of the cardiovascular system is the brain, the liver, a kidney, one or more carotid arteries, or any other part of the cardiovascular system.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit, processor, or device may fulfill the functions of several items recited in the claims. The mere fact that certain measures are recited in mutually different dependent claims does not indicate that a combination of these measures cannot be used to advantage.

Operations like receiving X-ray image data, generating a segmented model, extracting features, calculating inflammation values, calculating probability values, visualizing inflammation values, visualizing inflammation values together with the segmented model, generating a view, generating different views, suggesting actions, performing actions, et cetera performed by one or several units or devices can be performed by any other number of units or devices. These operations and/or the image data analysis device or image data analysis system can be implemented as program code means of a computer program and/or as dedicated hardware.

A computer program may be stored/distributed on a suitable medium, such as an optical storage medium, or a solid-state medium, supplied together with or as part of other hardware, but may also be distributed in other forms, such as via the Internet, Ethernet, or other wired or wireless telecommunication systems.

Any reference signs in the claims should not be construed as limiting the scope.

The present invention relates to X-ray image data analysis of a part of a cardiovascular system of a patient in order to estimate a level of inflammation in the part of the cardiovascular system. X-ray image data is received, a segmented model of the part of the cardiovascular system is generated and predetermined features related to inflammation are extracted from the segmented model. The extracted features are used as input to an inflammation function for calculating inflammation values of which each represents a level of inflammation in the part of the cardiovascular system. The image data analysis can improve the estimation of inflammation. Furthermore, the inflammation values can be presented to a user together with suggestions for performing actions. This can for example enable a prediction of plaque development as well as future acute coronary syndrome events.

The invention claimed is:

1. An image data analysis device for analyzing X-ray image data of a part of a cardiovascular system of a patient in order to estimate a level of inflammation in the part of the cardiovascular system, comprising:
a non-transitory memory configured to store instructions; and
a processor configured to execute the instructions that cause the image data analysis device to:
receive the X-ray image data comprising the part of the cardiovascular system of the patient;
generate a segmented model of the part of the cardiovascular system from the X-ray image data as an anatomical model, wherein the segmented model comprises segments that have different elements, density and/or thickness;
design predetermined features;
extract the predetermined features related to inflammation from the segmented model, wherein the predetermined features are extracted based on pattern-recognition performed on the segmented model;
combine the extracted and designed predetermined features into a vector; and
calculate inflammation values of an inflammation function depending on the extracted and designed features, wherein the vector is an input to the inflammation function, and wherein each of the inflammation values represents a level of inflammation in the part of the cardiovascular system.

2. The image data analysis device according to claim 1, wherein the inflammation function is optimized by machine learning methods.

3. The image data analysis device according to claim 2, wherein the inflammation function is optimized in dependence of training data comprising histology analysis data, disease outcome data, and/or data received from medical imaging techniques allowing to estimate the level of inflammation.

4. The image data analysis device according to claim 1, wherein the processor is further configured to visualize the inflammation values or the inflammation values together with the segmented model, and generate different views based on the inflammation values.

5. The image data analysis device according to claim 1, wherein the image data is spectral computed tomography data.

6. The image data analysis device according to claim 1, wherein the processor is further configured to estimate a probability for development of plaque in the part of the cardiovascular system and/or a probability for rupturing of plaque in the part of the cardiovascular system based on the inflammation values.

7. The image data analysis device according to claim 1, comprising a user interface configured to provide an interaction between a user and the image data analysis device, wherein the user interface is configured to provide suggestions for actions in dependence of the inflammation values.

8. A method for analyzing X-ray image data of a part of a cardiovascular system of a patient in order to estimate a level of inflammation in the part of the cardiovascular system, the method comprising:
receiving X-ray image data comprising the part of the cardiovascular system of the patient;
generating a segmented model of the part of the cardiovascular system from the image data as an anatomical model, wherein the segmented model comprises segments that have different elements, density and/or thickness;
designing predetermined features;
extracting the predetermined features related to inflammation from the segmented model by performing pattern-recognition on the segmented model;
combining the extracted and designed predetermined features into a vector; and
calculating inflammation values of an inflammation function depending on the extracted and designed features, wherein the vector is an input to the inflammation function, and wherein each of the inflammation values represents a level of inflammation in the part of the cardiovascular system.

9. The method according to claim 8, further comprising visualizing the inflammation values or the inflammation values together with the segmented model, wherein different views based on the inflammation values can be generated.

10. A non-transitory computer-readable medium having one or more executable instructions stored thereon which, when executed by at least one processor, cause the at least one processor to perform a method for analyzing X-ray image data of a part of a cardiovascular system of a patient in order to estimate a level of inflammation in the part of the cardiovascular system, the method comprising:
receiving X-ray image data comprising the part of the cardiovascular system of the patient;
generating a segmented model of the part of the cardiovascular system from the image data as an anatomical model, wherein the segmented model comprises segments that have different elements, density and/or thickness;
designing the predetermined features;
extracting the predetermined features related to inflammation from the segmented model by performing pattern-recognition on the segmented model;
combining the extracted and designed predetermined features into a vector; and
calculating inflammation values of an inflammation function depending on the extracted and designed features, wherein the vector is an input to the inflammation function, and wherein each of the inflammation values represents a level of inflammation in the part of the cardiovascular system.

11. The image data anaylysis system according to claim 10, comprising a training device configured to optimize the inflammation function of the image data analysis device.

12. The image data analysis system according to claim 11, wherein the training device is configured to optimize the inflammation function in dependence of training data, and wherein the training data comprises histology analysis data, disease outcome data, and/or data received from medical imaging techniques allowing to estimate the level of inflammation.

* * * * *